United States Patent
Sumiya et al.

(10) Patent No.: US 10,126,112 B2
(45) Date of Patent: Nov. 13, 2018

(54) TOMOGRAPHIC IMAGE CAPTURING APPARATUS AND METHOD WITH NOISE REDUCTION TECHNIQUE

(71) Applicant: CANON KABUSHIKI KAISHA, Tokyo (JP)

(72) Inventors: Toshiharu Sumiya, Kawasaki (JP); Makoto Fukuhara, Yokohama (JP); Makoto Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 64 days.

(21) Appl. No.: 14/870,959

(22) Filed: Sep. 30, 2015

(65) Prior Publication Data

US 2016/0097632 A1  Apr. 7, 2016

(30) Foreign Application Priority Data

Oct. 7, 2014  (JP) .................................. 2014-206374

(51) Int. Cl.
*G01B 9/02* (2006.01)
*A61B 3/10* (2006.01)

(52) U.S. Cl.
CPC .......... *G01B 9/02091* (2013.01); *A61B 3/102* (2013.01); *G01B 9/02044* (2013.01); *G01B 9/02059* (2013.01); *G01B 9/02064* (2013.01)

(58) Field of Classification Search
CPC ............ G01B 9/02091; G01B 9/02044; G01B 9/02064; G01B 9/02059; A61B 3/102
See application file for complete search history.

(56) References Cited

U.S. PATENT DOCUMENTS

2006/0279742 A1* 12/2006 Tearney ............... A61B 5/0066
356/498
2007/0276269 A1* 11/2007 Yun ........................ A61B 3/102
600/504

(Continued)

FOREIGN PATENT DOCUMENTS

JP  2000329514 A  11/2000
JP  2008545970 A  12/2008

(Continued)

OTHER PUBLICATIONS

Fercher et al, "Measurement of intraocular distances by backscattering spectral interferometry", Optics Communications, 117, 1995, pp. 43-48.

(Continued)

*Primary Examiner* — Michael P Lapage
(74) *Attorney, Agent, or Firm* — Carter, DeLuca, Farrell & Schmidt, LLP (57) ABSTRACT

An object is to enable removal fixed pattern noise even if the intensity of interference light changes during measurement. An image capturing apparatus comprises a light splitting unit that splits light emitted from a light source into reference light and measurement light, an interference signal detection unit that acquires an interference signal from interference light resulting from interference of the reference light and return light generated by irradiating an object to be inspected with the measurement light, a noise signal acquisition unit that acquires a noise signal containing a noise component contained in the interference light, a correction unit that corrects the intensity of one of the interference signal and the noise signal, and a noise removal unit that removes the noise component contained in the interference signal using the interference signal and the noise signal one of which is corrected.

21 Claims, 8 Drawing Sheets

(56) References Cited

U.S. PATENT DOCUMENTS

| | | | |
|---|---|---|---|
| 2013/0208968 A1* | 8/2013 | Hanebuchi | G06T 5/002 |
| | | | 382/131 |
| 2014/0176961 A1* | 6/2014 | Johansson | G01B 9/02072 |
| | | | 356/479 |
| 2014/0221827 A1* | 8/2014 | Motaghiannezam | |
| | | | G01N 21/4795 |
| | | | 600/425 |

FOREIGN PATENT DOCUMENTS

| | | |
|---|---|---|
| JP | 2009523564 A | 6/2009 |
| JP | 2011069716 A | 4/2011 |
| JP | 2011-242177 A | 12/2011 |
| JP | 2014016318 A | 1/2014 |
| JP | 2014155694 A | 8/2014 |

OTHER PUBLICATIONS

Moon et al., "Reference spectrum extraction and fixed-pattern noise removal in optical coherence tomography", Optics Express, vol. 18, No. 23, 2010, pp. 24395-24404.

Japanese Office Action dated Jun. 21, 2018 in corresponding Japanese Patent Application No. 2014-206374, together with English translation (12 pages).

* cited by examiner

TOMOGRAPHIC IMAGE CAPTURING APPARATUS AND METHOD WITH NOISE REDUCTION TECHNIQUE

BACKGROUND OF THE INVENTION

Field of the Invention

The present invention relates to an image capturing apparatus that captures a tomographic image of an object to be inspected by optical coherence tomography and a noise removal method and noise removal program for tomographic images.

Description of the Related Art

Image capturing apparatuses based on optical coherence tomography (OCT) utilizing interference of low coherent light are well known. (Such an apparatus will be hereinafter referred to as an OCT apparatus). The OCT apparatus can generate a tomographic image of an object to be inspected with high resolution.

The OCT apparatus splits light from a light source into measurement light and reference light by means of a beam splitter or the like. The measurement light is delivered to an object to be inspected such as an eye, and the measurement light is reflected and diffused by the object to be inspected. The resulting return light from the object to be inspected is combined with the reference light having passed through a reference mirror, and guided to a detector. The return light has information about the layers in the object to be inspected in the irradiation direction. Interference light of the return light and the reference light is detected by the detector. A tomographic image of the object to be inspected is acquired by analyzing the interference signal thus obtained.

A. F. Fercher, C. k. Hitzenberger, G. Kamp, S. Y. El-Zaiat, Opt, Commun. 117, 43-48, (1995) disclose a Fourier domain OCT apparatus (which will be hereinafter referred to as FD-OCT apparatus), which obtains wavelength spectrum with a fixed reference mirror and performs tomographic measurement by Fourier-transforming the wavelength spectrum. The FD-OCT apparatuses include SD-OCT (spectral domain-OCT) apparatuses using a spectrometer and SS-OCT (swept source-OCT) apparatuses that sweep the wavelength of the light source.

In tomographic imaging of an object to be inspected with an OCT apparatus, the spectral intensity distribution of the reference light is also Fourier-transformed. Consequently, intensity information of each frequency component appears as noise in the image. Moreover, in cases where multiple reflection occurs in the optical system, frequency components resulting from interference with multiple-reflected light are generated. In this case also, noise resulting from such frequency components appears in the image.

According to a known method of removing such noise, information about the spectral intensity distribution of the light source is obtained in advance by measurement to remove noise (see S. Moon, S. W. Lee, Z. Chen, Optics Express, Vol. 18, No. 23, 24395-24404, (2010)). However, in cases where the intensity of light emitted from the light source is unstable or where the light quantity changes due to the transmittance of optical components, vibration of optical components, temperature changes, and/or other factors, the noise intensity also changes, so that residual noise remains unremoved.

An apparatus disclosed in Japanese Patent Application Laid-Open No. 2011-242177 is intended to remove such noise. This apparatus is provided with a system for detecting a reference light signal for correction separately from a system for detecting a reference signal obtained by interference of reference light and measurement light. These systems detect the interference signal and the reference light signal separately from each other, so that the interference signal is corrected by the reference light signal. By this technique, the interference signal and the correction signal are measured concurrently. This enables removal of noise even if the light quantity of the reference light changes (or the light quantity of the interference signal changes).

The apparatus disclosed in Japanese Patent Application Laid-Open No. 2011-242177 is required to have an additional optical system and an additional detector for the purpose of obtaining the reference light signal for correction. Moreover, it is necessary that the light quantity of the interference light and the light quantity of the reference light signal for correction be adjusted to be balanced among the detectors. Therefore, the construction of the apparatus and the adjustment process are complex.

SUMMARY OF THE INVENTION

The present invention has been made in view of the above-described circumstances. The present invention is to provide an image capturing apparatus such as an OCT apparatus that is not complex but simple in construction and capable of reducing noise even when the light quantity of interference signal changes, and to provide a noise removal method and noise removal program for tomographic images.

To achieve the above problem, according to the present invention, there is provided an image capturing apparatus comprising a light splitting unit that splits light emitted from a light source into reference light and measurement light, an interference signal detection unit that acquires an interference signal from interference light resulting from interference of the reference light and return light generated by irradiating an object to be inspected with the measurement light, a noise signal acquisition unit that acquires a noise signal containing a noise component contained in the interference light, a correction unit that corrects the intensity of one of the interference signal and the noise signal, and a noise removal unit that removes the noise component contained in the interference signal using the interference signal and the noise signal one of which is corrected.

According to the present invention, a tomographic image of an object to be inspected with reduced noise can be captured by a simple apparatus even when the light quantity of an interference signal changes.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

Figure 2:
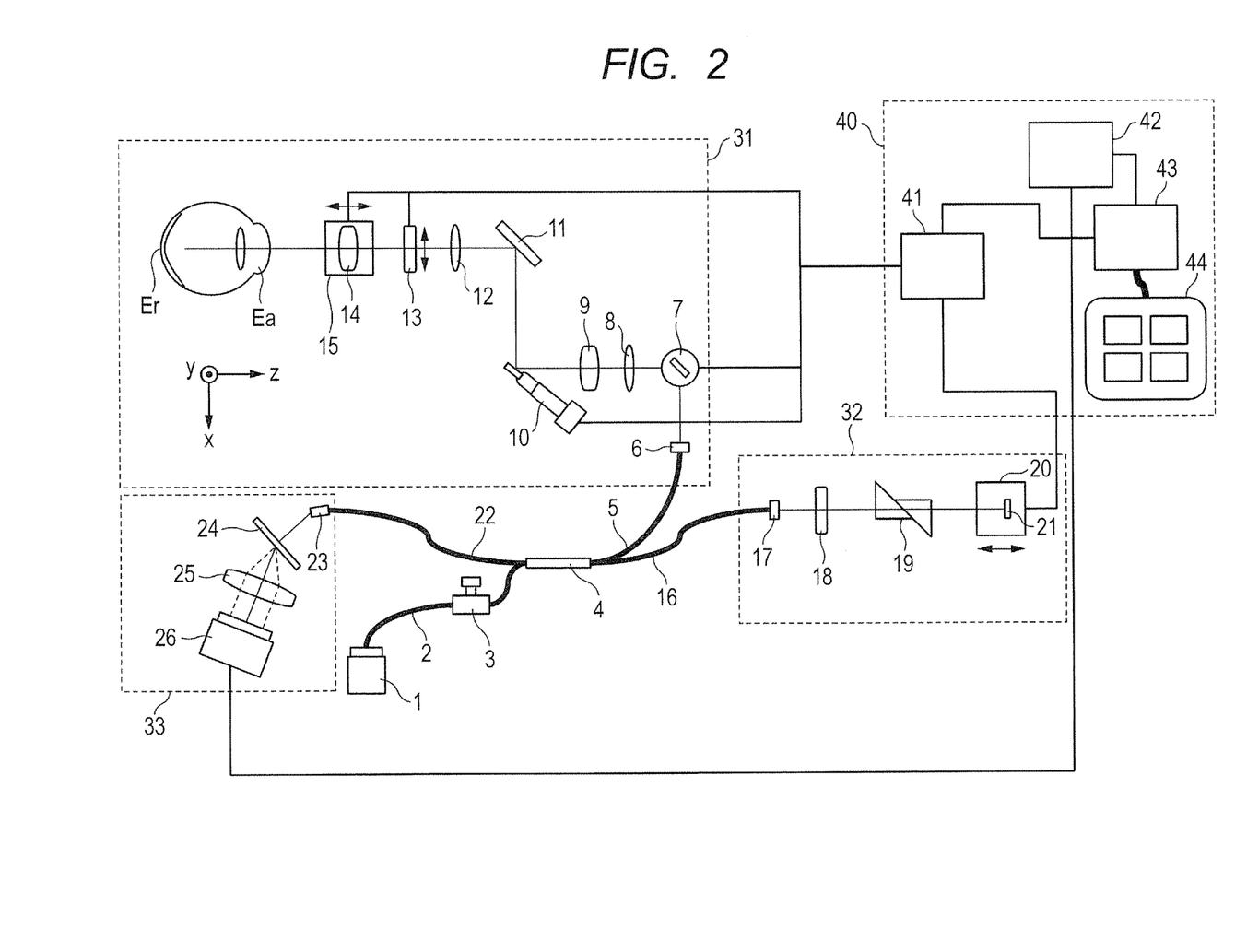
FIG. 2 is a diagram schematically illustrating the overall configuration of an image processing apparatus in the first embodiment of the present invention.

FIG. 2 shows an exemplary configuration of an optical coherence tomography image capturing apparatus (OCT apparatus) according to an embodiment of the present invention. The OCT apparatus has a light source 1, a fiber coupler 4, a sample arm (measurement optical path) 31, a reference arm (reference optical path) 32, a spectrometer 33, and a control apparatus 40. In the embodiment described here, the image capturing apparatus employs Fourier-domain optical coherence tomography, and a case where a tomographic image of the fundus of an eye as an object to be inspected (examined object) will be described. The examined object is not limited to the eye fundus, but the OCT apparatus may generate a tomographic image of, for example, human skin.

The light source 1 is a super luminescent diode (SLD), which is a low coherent light source and emits light with the center wavelength of 850 nm and a bandwidth of 50 nm. In this embodiment, an SLD is used as the light source 1. Alternatively, the light source 1 may be any other light source that can emit low coherent light. For example, an amplified spontaneous emission (ASE) light source may be employed. The aforementioned values of the center wavelength and the bandwidth are given by way of example, and their values are not limited to them.

Light emitted from the light source 1 is guided to the fiber coupler 4 through a fiber 2, and a polarization controller 3 and split into measurement light and reference light. In this embodiment, the fiber coupler 4 constitutes light splitter that splits the light emitted from the light source into reference light and measurement light. The polarization controller 3 controls the polarization of the light emitted from the light source 1. The polarization is controlled in such a way that interference of the measurement light and the reference light is enhanced.

The split ratio of the fiber coupler 4 is 90 (reference light): 10 (measurement light). The value of the split ratio is not limited to this, but it may be set to other values. The measurement light after splitting is introduced into the sample arm 31 through a fiber 5 and emitted from a collimator 6 as parallel light. Thereafter, the measurement light passes through an X scanner 7, lenses 8 and 9, and a Y scanner 10 and enters a mirror 11. The X scanner 7 and the Y scanner 10 are controlled by a drive control unit 41. The X scanner 7 and the Y scanner 10 are galvanometer mirrors, by which the eye fundus Er is scanned with the measurement light in the horizontal and vertical directions respectively. A desired range of region of the eye fundus Er can be scanned with the measurement light by controlling these scanners. The measurement light reflected by the mirror 11 passes through a lens 12.

A shutter 13 is provided in the optical path of the measurement light. The shutter 13 can be inserted into/retracted out of the optical path. The shutter 13 is controlled by the drive control unit 41. When an image of the examined object is taken, the shutter 13 is retracted out of the optical path of the measurement light. When the measurement light is to be blocked, the drive control unit inserts the shutter 13 into the optical path of the measurement light.

The measurement light is focused by a focus lens 14 provided on a stage 15 onto retina layers of the eye fundus Er through the anterior ocular segment Ea of the eye as the examined object. The measurement light with which the eye fundus Er is irradiated is reflected and diffused by the retina layers to return to the fiber coupler 4 through the above-described optical path in the reverse direction.

The reference light split by the fiber coupler 4 is introduced into the reference arm 32 through a fiber 16 and emitted from a collimator 17 as parallel light. The reference light passes through an ND filter 18 for controlling the light quantity and a dispersion compensating glass 19 and is reflected by a mirror 21 provided on a coherence gate stage 20 to return to the fiber coupler 4. The coherence gate stage 20 is adapted to accommodate variations in the axial length of the eye among the examinees. The position of the coherence gate stage 20 with respect to the optical axis direction is controlled by the drive control unit 41.

The measurement light and the reference light returning to the fiber coupler 4 are combined to form interference light. The reference light is delivered to the spectrometer 33 through a fiber 22. In the spectrometer 33, the interference light is transmitted through a collimator 23, separated into spectral components by a grating 24, transmitted through a lens 25, and received by a line camera 26. The light received by the line camera 26 is converted into an electrical signal representing the light intensity and output from the line camera 26. The output electrical signal is received by a signal processing unit 42. The section including the spectrometer 33, the line camera 26, and the signal processing unit 42 in this embodiment constitutes an interference signal detector that acquires an interference signal resulting from the interference of the reference light and the return light (or back-reflected light) resulting from irradiation of the examined object with the measurement light. These components also function as a noise signal acquisition unit that acquires a noise single having noise components contained in the interference light.

Now, the control apparatus 40 will be described. The control apparatus 40 includes the drive control unit 41, the signal processing unit 42, a control unit 43, and a display unit 44.

As described above, the drive control unit 41 controls actuators of the scanners 7, 10 and the stages 15, 20.

The signal processing unit 42 generates an image based on the electrical signal output from the line camera 26, analyzes the image thus generated, and generates data for visualizing the result of the analysis. Details of the process of generating the image will be described later.

The control unit 43 performs overall control of the apparatus and displays images generated by the signal processing unit 42 on a display screen of the display unit 44. The display unit 44 displays various information under the control of the control unit 43, as will be described later. The display unit 44 is, for example, a liquid crystal display. The image data generated by the signal processing unit 42 may be transmitted to the control unit 43 by either wired or wireless communication. In this case, the control unit 43 may be regarded as an image processing apparatus.

The signal processing unit 42 applies reconstruction processing employed in the SD-OCT to the interference signal input from the line camera 26 to generate a tomographic signal. The interference light of the return light from the eye fundus Er as the examined object and the reference light from the reference mirror 21 has a phase difference resulting from the difference between the optical path length from the fiber coupler 4 to the eye fundus Er and the optical path length from the fiber coupler 4 to the reference mirror 21. Because this phase difference varies depending on the wavelength, the spectral intensity distribution appearing on the line camera 26 by the interference light has interference fringes (interference signal). The brightness at a position of a reflecting object can be determined by determining the period of the intensity distribution (or interference fringes).

Figure 3A:
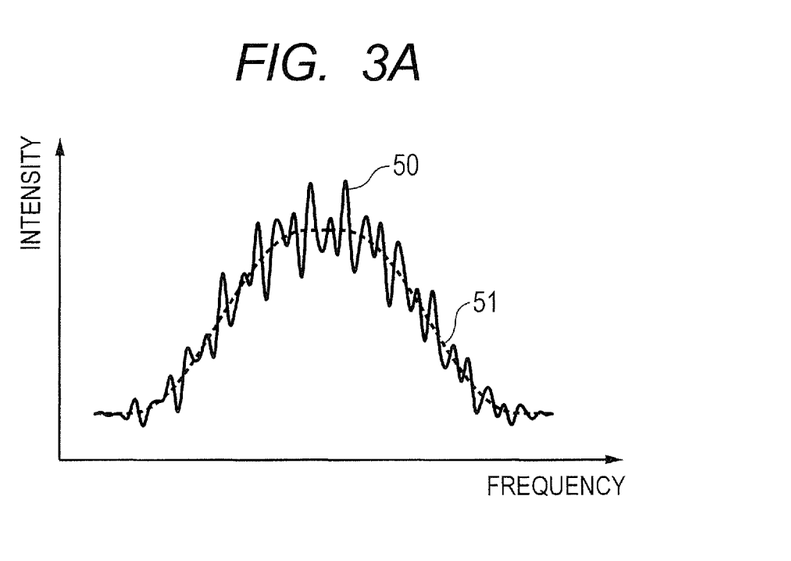
FIG. 3A shows an exemplary interference signal in optical coherence tomography.
Figure 3B:
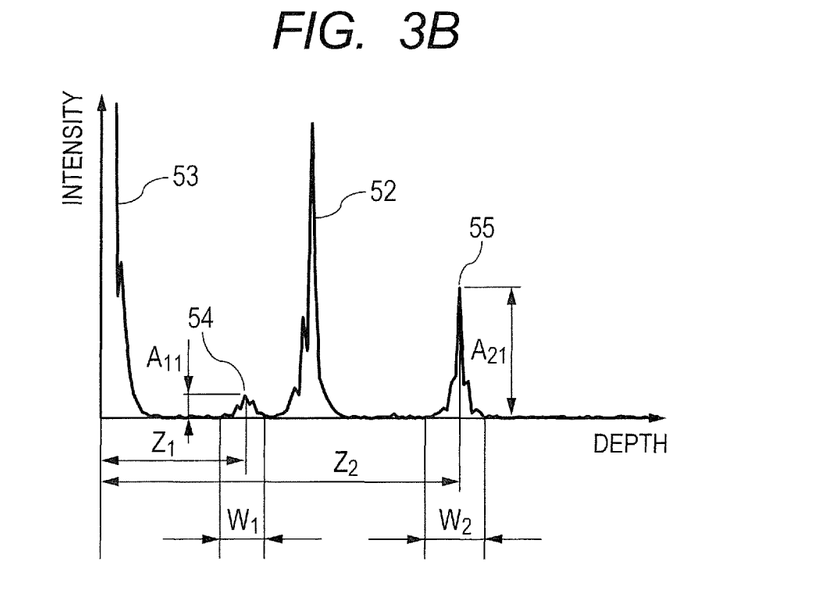
FIG. 3B shows an exemplary interference tomographic signal.

Noise components contained in the signal (interference signal) received by the above-described line camera 26 will be discussed. FIG. 3A schematically shows an example of the interference signal (or intensity distribution of interference fringes) detected by the line camera 26. FIG. 3B schematically shows an example of a tomographic signal obtained by Fourier-transforming the interference signal. FIG. 3A shows the variation of the spectral intensity in relation to the frequency. FIG. 3B shows the variation of the spectral intensity along the depth direction of the examined object. The interference signal 50 (solid curve) contains an interference component representing the shape of the examined object, a component of a waveform 51 (broken curve) representing the spectral intensity distribution of the light source 1, and interference components resulting from multiple reflection or the like in the optical path. When obtaining intensity information for each frequency component, an intensity distribution other than the interference component with the return light contained in the interference light will deteriorate image quality as noise. Noise resulting from multiple reflection of the like in the optical path is called fixed pattern noise (FPN).

In the case of the tomographic signal shown in FIG. 3B, a noise 53 attributed to autocorrelation and fixed pattern noises 54, 55 are superposed on the tomographic signal 52 attributed to the examined object.

In cases where the intensity of the light source is not stable or where the light quantity of the interference signal varies due to the transmittance of optical components, vibration of optical components, temperature changes, and/or other factors, the intensity of the noise changes. In research conducted by the inventors, variation of the light quantity was observed as a vibration of 0.1 to several Hz or a drift of a longer period, and the range of variation was ±20% of the average value. The range of variation and the period depend on the construction of the OCT apparatus and environment. Therefore, they are not necessarily constant.

Figure 1:
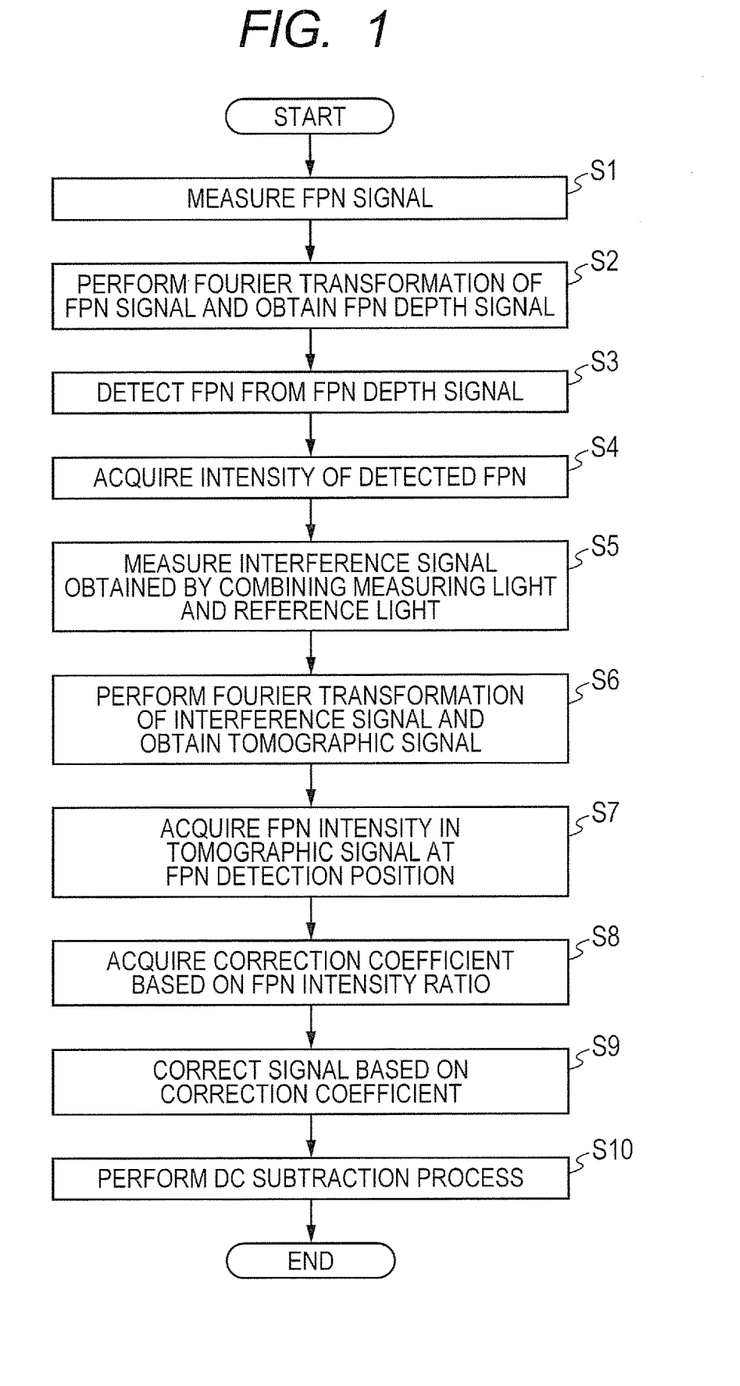
FIG. 1 is a flow chart of processing in a first embodiment of the present invention.

FIG. 1 is a flow chart of a process of removing noise in the OCT apparatus according to the first embodiment. The noise removing process includes acquisition and analysis of a fixed pattern noise signal and an interference signal, signal correction, and noise removal. The process of this flow chart is started after positional alignment and adjustment of focus and coherence gate for the examined object have been finished. In the description of this and other embodiments, we use the expressions "removal of noise", "removing noise" or the like. However, it is difficult to make noise actually and completely suppressing. The expressions "removal of noise" and "removing noise" mean reducing noise to a level at which its effect is negligible in signal processing.

Firstly, a fixed pattern noise signal (FPN signal) of the OCT apparatus is measured (S1). The FPN signal can be obtained by measuring the intensity distribution of light that travels from the reference optical path and the measurement optical path to the line camera 26 in a state in which the measurement light is shut off. The light that travels from the reference optical path to the line camera 26 includes not only the reference light reflected by the mirror 21 but also light reflected by components provided in the reference optical path (e.g. the ND filter 18 and the dispersion compensation glass 19 etc.). The light that travels from the measurement optical path to the line camera 26 also includes light reflected by components provided in the measurement optical path (e.g. lenses 8, 9, 12 etc.). In order to reduce the influence of variation of the light quantity, it is desirable that the FPN signal be averaged over a sufficiently long measurement time (the times of measurements) as compared to the period of variation of the light quantity. To shut off or block the measurement light, blocking means such as the shutter 13 may be controlled to be inserted into the optical path of the measurement light. Alternatively, a scanner may be controlled to displace the measurement light away from the examined object to prevent the measurement light from being detected by the line camera 26. Specifically, a reflector such as a scanner may be provided in the optical path of the measurement light to displace the measurement light away from the examined object so that the measurement light is not detected by the line camera 26. The shutter is provided in order to reduce (to zero, ideally) the measurement light travelling to the line camera 26 by absorbing or diffusing the measurement light.

In the above-described example, the shutter 13 is used for measurement of the FPN signal. However, means for reducing the measurement light travelling to the line camera 26 is not limited to this. For example, light may be emitted from the light source 1 without using the shutter 13 in a state in which an examined eye is not opposed to the OCT apparatus (without an examined eye in place), and the FPN signal may be measured based on light received by the line camera 26 in this state. With this method, noise attributed to light reflected by the focus lens 14 in the measurement optical path can also be contained in the FPN signal, enabling noise reduction with improved accuracy. In the case where the shutter 13 is not used, noise attributed to light reflected by an objective lens, which is not is illustrated in FIG. 2, can also be contained in the FPN signal.

In the case where the shutter 13 is used for the above-described purpose, it is preferred that the shutter be inserted into the measurement optical path at a position as close as possible to the examined eye, so that more noise components are contained in the FPN signal. For example, the shutter 13 is inserted in the measurement optical path at a position adjacent to the objective lens (not shown), which is located closest to the examined eye among the optical elements, on the side opposite to the examined eye. In other words, the shutter 13 is inserted between the objective lens (not shown) and the focus lens 14.

The measurement of the FPN signal may be performed in the calibration process started at the time when the OCT apparatus is turned on or performed at the time when the examinee changes. At the time when the OCT apparatus is turned on or when the examinee changes, it is probable that the examined eye is not opposed to the OCT apparatus, and therefore it is preferred that the measurement of the FPN signal without using the shutter 13 be performed at that time.

Figure 4A:
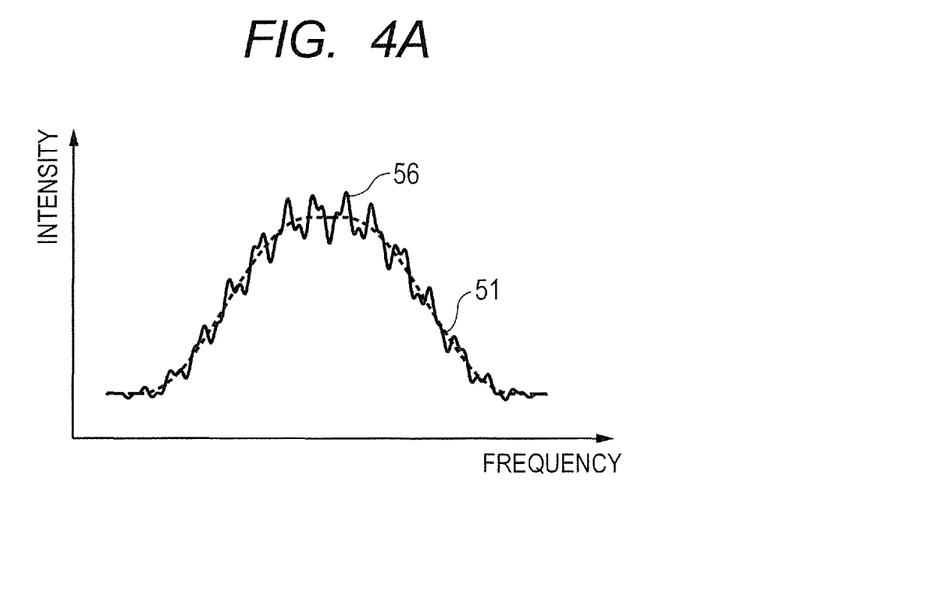
FIG. 4A shows an exemplary interference signal of fixed pattern noise in optical coherence tomography.

FIG. 4A shows an exemplary intensity distribution of the measured FPN signal. The FPN signal 56 (solid curve) contains the component 51 (broken curve) of a waveform representing the spectral intensity distribution of the light source 1 and interference components attributed to multiple reflection in the optical path.

Figure 4B:
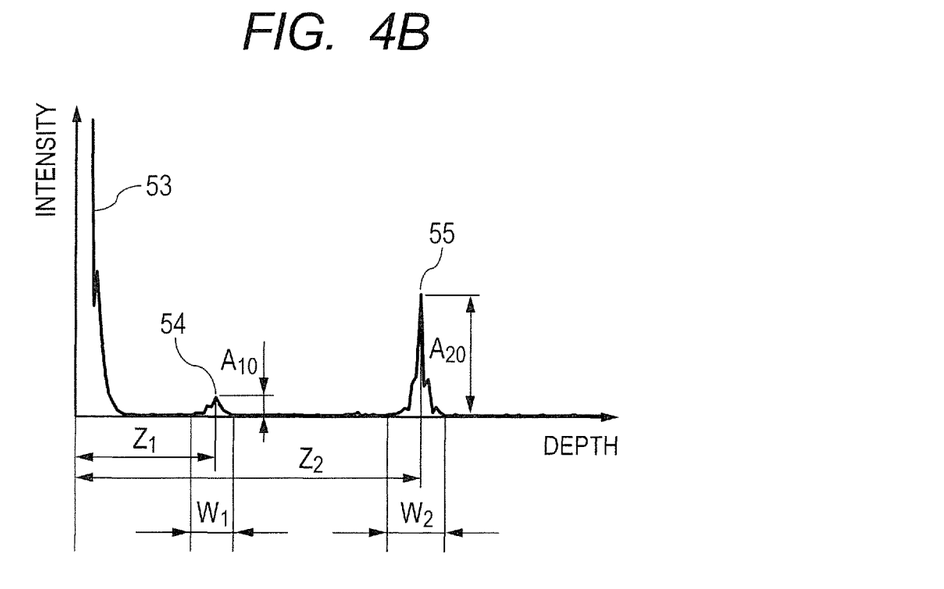
FIG. 4B shows an exemplary interference tomographic signal.

Then, the FPN signal is Fourier-transformed by the signal processing unit 42 into a depth signal (FPN tomographic signal) (S2). FIG. 4B shows an example of the FPN tomographic signal. In this embodiment, the signal processing unit 42 constitutes signal processing means that Fourier-transforms an interference signal and a noise signal to generate an interference tomographic signal and a noise tomographic signal (FPN tomographic signal).

Then, a noise 53 attributed to autocorrelation and fixed pattern noises 54, 55 are detected from the FPN tomographic signal (S3). After detecting the fixed pattern noises, the signal processing unit 42 memorizes the noise detection position with respect to the depth direction of the examined object (eye fundus) and the range of the detected noise. Specifically, the signal processing unit 42 as signal processing means determines the depth position of the noise component from the FPN tomographic signal and memorizes it.

A fixed pattern noise can be detected by a peak having a certain intensity corresponding to the fixed pattern noise. Since the portions other than the fixed pattern noise has substantially constant low intensity constituting white noise, the fixed pattern noise can easily be discerned. In the exemplary case shown in FIG. 4B, the peaks 54, 55 correspond to fixed pattern noises, and the detected positions $Z_1$, $Z_2$ correspond to the positions of the fixed pattern noises, and the detection ranges $W_1$, $W_2$ correspond to the ranges of the fixed pattern noises. In cases where the positions at which the fixed pattern noises appear and their ranges are known beforehand, the positions and the ranges may be specified in advance, and their data may be used in the detection.

Then, the intensity of each of the detected fixed pattern noises is acquired (S4). The signal processing unit 42 memorizes the intensities of the fixed pattern noises thus acquired. In the exemplary case shown in FIG. 4B, intensities $A_{10}$, $A_{20}$ are the intensities of the fixed pattern noises. Information on the fixed pattern noise thus obtained is used in signal correction processing and noise removal processing that will be described later.

Then, the drive control unit 41 causes the shutter 13 to retract from the optical path. Thereafter, measurement light is cast onto the examined object, and the intensity distribution of the interference signal in which the measurement light and the reference light are combined is measured (S5). As mentioned above, an example of the measured intensity distribution of the interference light is shown in FIG. 3A. A plurality of interference signals 50 for forming a tomographic image or a three-dimensional image may be obtained by scanning with the scanners.

Then, the interference signal is Fourier-transformed by the signal processing unit 42 into a depth signal (interference tomographic signal) (S6). As mentioned above, an example of the interference tomographic signal is shown in FIG. 3B. In the interference tomographic signal, a noise 53 attributed to autocorrelation and fixed pattern noises 54, 55 are superposed on the tomographic signal 52 attributed to the examined object.

Then, the intensities of the fixed pattern noises in the interference tomographic signal are acquired (S7). The intensities of the fixed pattern noises are obtained in portions corresponding to the positions and ranges of the fixed pattern noises detected in steps S3 and S4. In the case shown in FIG. 3B, obtained data correspond to the positions $Z_1$, $Z_2$, the ranges $W_1$, $W_2$, and the intensities $A_{11}$, $A_{21}$ of the fixed pattern noises.

Then, a correction coefficient is determined by comparing the intensities of the fixed pattern noises in the signal acquired in step S4 and the intensities of the fixed pattern noises in the signal acquired in step S7 (S8). An exemplary method of determining the correction coefficient will be described with reference to the exemplary interference tomographic signal shown in FIG. 3B and the exemplary FPN tomographic signal shown in FIG. 4B. In the example shown in FIG. 3B, the intensities of the fixed pattern noises superposed on the interference tomographic signal are represented by $A_{11}$ and $A_{21}$. In the example shown in FIG. 4B, the intensities of the fixed pattern noises are represented by $A_{10}$ and $A_{20}$. The correction coefficient α is determined by the following equation 1:

$$\alpha = \left(\sum_{n=1}^{N} \alpha_n\right)/N = \left(\sum_{n=1}^{N} \frac{A_{n1}}{A_{n0}}\right)/N, \quad \text{(equation 1)}$$

where N is the number of the detected fixed pattern noises, $A_{n0}$ is the intensity of the n-th fixed pattern noise in the FPN tomographic signal, $A_{n1}$ is the intensity of the n-th fixed pattern noise superposed on the interference tomographic signal, $\alpha_n$ is the correction coefficient for the n-th fixed pattern noise. The correction coefficient α is calculated as the average of the correction coefficients $\alpha_n$ of the N fixed pattern noises, as expressed by equation 1. In other words, in cases where there are a plurality of noise components in the FPN signal, it is desirable that the correction coefficient actually used in correcting the interference tomographic signal be calculated from a plurality of correction coefficients corresponding to the respective noise components. The correction coefficient α corresponds to the difference between the light quantity at the time when the FPN signal is acquired and the light quantity at the time when the interference signal is acquired.

Then, signal correction using the correction coefficient is performed (S9). In the signal correction, for example, the FPN tomographic signal is corrected according to the following equation 2:

(FPN tomographic signal)new=α×(FPN tomographic
    signal)     (equation 2), where "(FPN tomographic signal)" is the FPN tomographic signal before correction, and "(FPN tomographic signal) new" is the FPN tomographic signal after correction.

Figure 5A:
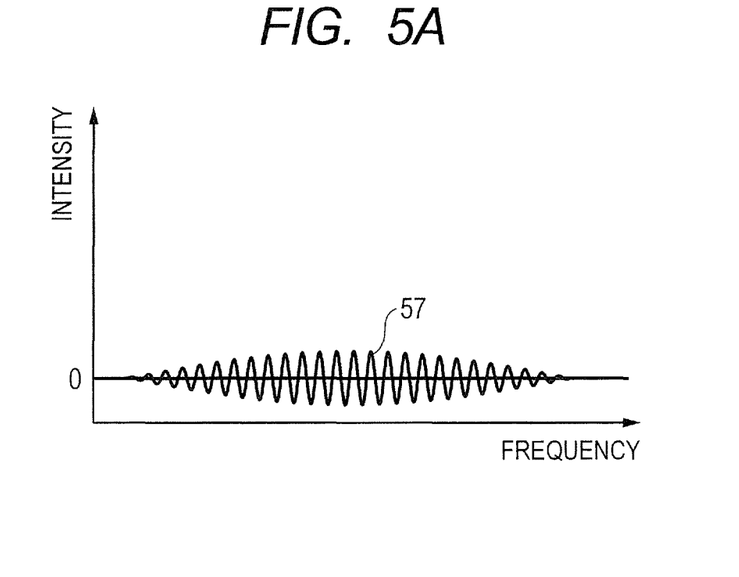
FIG. 5A shows an exemplary interference signal after removal of fixed pattern noise in a first embodiment of the present invention.
Figure 5B:
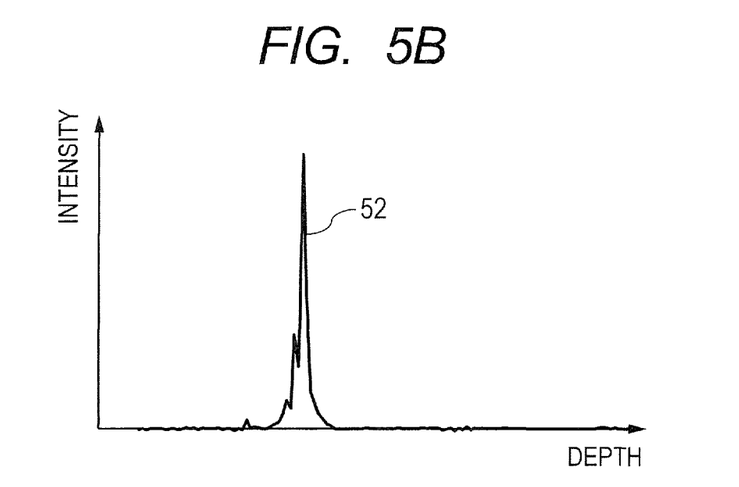
FIG. 5B shows an exemplary interference tomographic signal.

Finally, DC subtraction is performed, in which the FPN tomographic signal after correction is subtracted from the interference tomographic signal (S10). An example of the interference tomographic signal after the DC subtraction is shown in FIG. 5B. Since correction adapted to the difference between the light quantity at the time when the FPN signal is acquired and the light quantity at the time when the interference signal is acquired is performed, signals derived from fixed pattern noises can be removed as shown in FIG. 5B.

By applying the above-described processing to each tomographic signal, fixed pattern noises can be removed even if the light quantity changes during picking-up of a tomographic image (B-scan) or a three-dimensional image (C-scan).

The above-described correction of one of the interference signal and the noise signal is executed by a module area in the signal processing unit 42 that functions as correction means. The DC subtraction that removes noise components contained in the interference signal using the interference signal and the noise signal, one of which is corrected, is executed by a module area in the signal processing unit 42 that functions as noise removal means.

In the following, a modification of the process described in the flow chart in FIG. 1 will be described.

While in the process shown in FIG. 1, the signal correction in step S9 and the DC subtraction in step S10 are applied to a tomographic signal, the signal correction and the DC subtraction may be applied to a signal before Fourier transform. FIG. 5A shows an example in a case where the DC subtraction is applied to a signal before Fourier transform. FIG. 5A shows relationship between the frequency of measurement light and the spectral intensity. The interference signal 57 after undergoing the DC subtraction has negative components also.

Correction and noise removal processing may also be performed for the noise 53 attributed to autocorrelation in the same manner in addition to the fixed pattern noise.

The determination of the correction coefficient and correction may be performed for each fixed pattern noise. Specifically, a correction coefficient $\alpha_n$ (the suffix "n" indicates connection with the n-th fixed pattern noise) may be determined for each of the fixed pattern noises in step S8. In this case, for the range $W_n$ corresponding to each fixed pattern noise, the FPN tomographic signal is corrected using the corresponding correction coefficient $\alpha_n$. Thus, in the case where the noise signal contains a plurality of noise components, it is preferred that the correction unit determine a correction coefficient for each of the noise components and perform correction for each of the noise components.

Performing correction for each of the fixed pattern noises enables refined removal of the fixed pattern noises.

In cases where a correction coefficient $\alpha_n$ for a fixed pattern noise calculated in step S8 exceeds a predetermined threshold, the corresponding correction coefficient may be excluded from the calculation of the correction coefficient. Specifically, for example, the overall correction coefficient $\alpha$ may be calculated by averaging the correction coefficients $\alpha_n$ exclusive of the correction coefficients of the fixed pattern noises exceeding the threshold in the calculation by equation 1.

In the case where correction is performed for each fixed pattern noise, a fixed pattern noise of which the correction coefficient exceeds the threshold may be corrected using the correction coefficient of the adjacent fixed pattern noise. In the case where a plurality of tomographic signals are acquired, like in the case of B-scan, the correction coefficient may be estimated from an adjacent tomographic signal. Setting a threshold for the correction coefficient can prevent overcorrection when an interference signal of the examined object is superposed on a fixed pattern noise.

The aforementioned threshold may be determined based on the largest change in the light quantity of the fixed pattern noises. The change in the light quantity varies depending on characteristics of the OCT apparatus, and therefore the value of the threshold may be determined by measuring the amount of change in advance. For example, in a case where the change in the light quantity is +20% of the average light quantity at largest, the threshold may be set to 1.2. The threshold may include a margin to allow for measurement errors. By setting the threshold based on the largest change in the light quantity in the OCT apparatus, correction can be adapted to the characteristics of the OCT apparatus, and overcorrection can be prevented from occurring. The values of the magnitude of change in the light quantity and the threshold are not limited to the values presented above, but they can be other values.

The signal corrected by the correction coefficient in step S9 may be an interference tomographic signal (or an interference signal). The interference tomographic signal may be corrected according to the following equation 3:

$$(\text{interference tomographic signal})\text{new} = 1/\alpha \times (\text{interference tomographic signal}) \quad \text{(equation 3)},$$

where "(interference tomographic signal)" is the intensity of the interference tomographic signal in the depth direction, and "(interference tomographic signal) new" is the signal intensity after correction. Thereafter, in step S10, DC subtraction is performed on the interference tomographic signal after correction using the FPN signal. By correcting the interference tomographic signal, correction of changes in the interference signal of the examined object can be achieved, in addition to removal of the fixed pattern noise.

The order of some of the processing steps shown FIG. 1 may be changed. For example, the acquisition of the FPN signal may be performed after the measurement of the interference signal. Specifically, the measurement of the interference signal in step S5 may be performed first, and thereafter the acquisition of the FPN signal and the analysis of the fixed pattern noise (S1 to S4) may be performed, and thereafter the analysis of the interference signal and the signal correction (S6 to S10) may be performed.

In the case where the FPN signal is obtained after the measurement of the interference signal, the FPN signal may be obtained from the interference signals for forming a tomographic image instead of measuring the FPN signal separately. For example, the FPN signal can be obtained by cancelling the interference components in the interference signals other than the fixed pattern noise by ensemble averaging of the interference signals. The ensemble averaging is averaging of signals along the A-scan direction. By this averaging, signals representing the structure of the examined eye are cancelled because of the randomness of the structure of the examined eye, and the FPN signal remains. Thus, the FPN signal can be obtained. A correction coefficient is determined for each tomographic signal by using the FPN signal, and correction and DC subtraction are performed. Obtaining the FPN signal from the interference signals enables correction with a shorter time interval between the interference signal and the FPN signal. Therefore, correction can be achieved even if the position at which the fixed pattern noise is generated changes every time the measurement of a tomographic image is performed.

In tomographic imaging by the OCT apparatus, if it can be considered that the change in the light quantity of the interference signal in one tomographic image is adequately small, determination of the correction coefficient and correction may be performed once for each tomographic image. For example, when a three-dimensional image is taken (C-scan) after the measurement of the FPN signal, determination of the correction coefficient and correction are performed once for each tomographic image. The correction coefficient may be determined, for example, by determining a correction coefficient for each of the interference tomographic signals for forming a tomographic image and averaging the correction coefficients thus determined. Alternatively, correction coefficients may be determined for representative interference tomographic signals. The representative signals may be, for example, tomographic signals at both ends and the center of the tomographic image. The correction coefficients falling out of a threshold may be excluded in averaging the correction coefficients. In this case, since the correction coefficient is determined based on a plurality of interference signals for forming a tomographic image, the correction coefficient can be determined stably. Alternatively, determination of the correction coefficient and correction processing may be performed for a plurality of divided regions of a tomographic image.

Figure 6A:
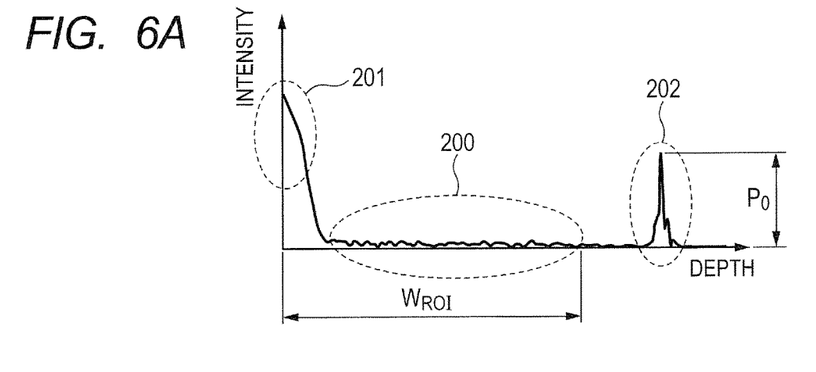
FIGS. 6A, 6B and 6C show exemplary interference tomographic signals in the first embodiment of the present invention.
Figure 6B:
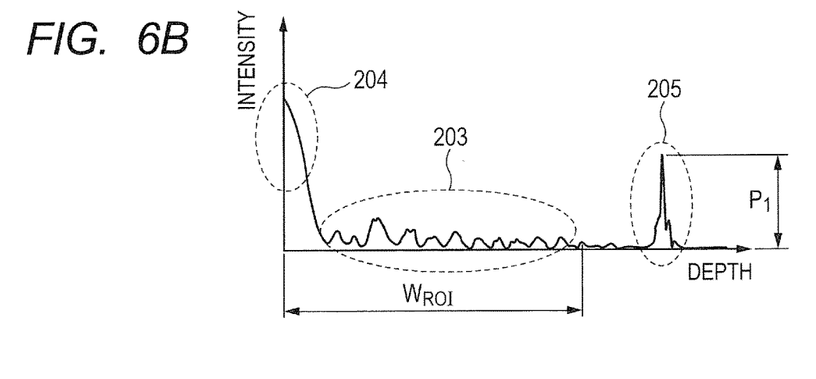
Figure 6C:
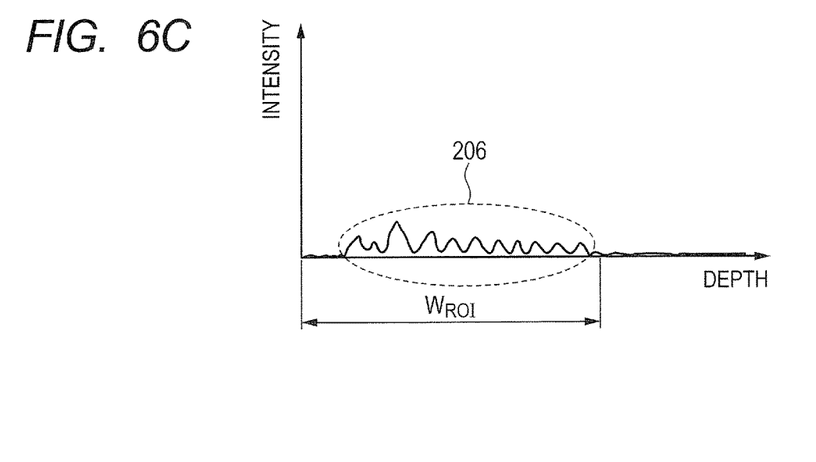
Figure 7:
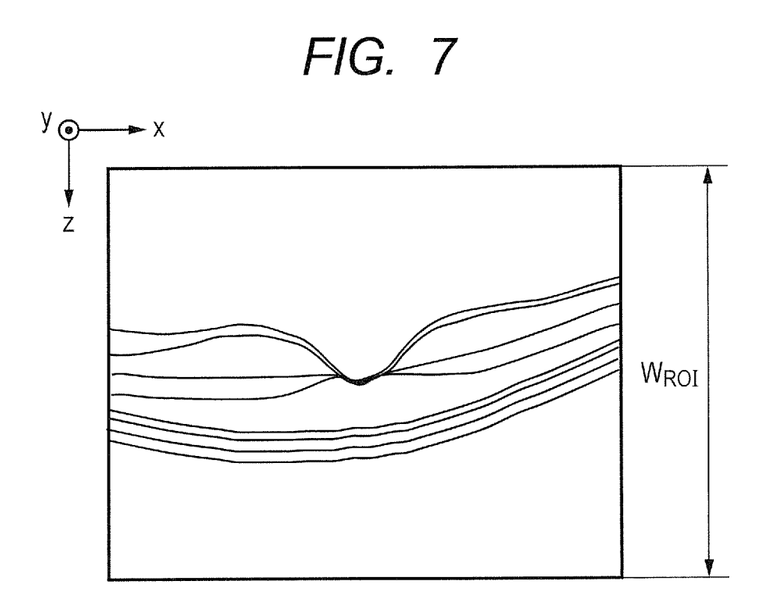
FIG. 7 shows an exemplary tomographic image in the first embodiment of the present invention.

A component that generates a fixed pattern noise may be provided in the optical path in order to determine the correction coefficient. For example, reflecting means that reflects a portion of light may be provided in the optical path of the OCT apparatus so that a fixed pattern noise appears outside the tomographic image display area. In this case, the reflecting means may be arranged, for example, between the collimator 17 and the mirror 21 in the reference arm 32. Thus, a fixed pattern noise can be detected when an interference signal tomographic image and an FPN tomographic image are acquired, and the fixed pattern noise appears in the image display area. In this mode, a translucent member such as a glass plate is used as the reflecting means. The position and thickness of the reflecting means are adjusted in such a way that a fixed pattern noise appears outside the tomographic image display area. For example, in a case where the upper end of the tomographic image display area corresponds to a position at which the difference between the optical path length of the reference optical path and the optical path length of the measurement optical path is equal to zero, the thickness of the glass plate is designed to be larger than the difference in the optical path length between the reference optical path and the measurement optical path corresponding to the height of the tomographic image display area. Thus, the fixed pattern noise can be made to appear inside the tomographic image display area. FIG. 6A shows an FPN tomographic image in this mode, and FIG. 6B shows an interference signal tomographic image in this mode. In FIGS. 6A and 6B, $W_{ROI}$ indicates the display area in the depth direction of the tomographic image. The FPN tomographic image shown in FIG. 6A contains fixed pattern noises 200 falling within the display area, an autocorrelation noise 201, and a fixed pattern noise 202 attributed to the reflecting means. The interference signal tomographic image shown in FIG. 6B contains a signal 203 in which fixed pattern noises are superposed on the interference signal of the examined object, an autocorrelation noise 204, and a fixed pattern noise 205 attributed to the reflecting means. In the fixed pattern noise 202, 205, the intensity of the interference tomographic signal of the examined object is relatively low. Therefore, the intensity $P_0$, $P_1$ of the fixed pattern noise attributed to the reflecting means can be determined with little effect of the interference light. Therefore, a correction coefficient having improved accuracy can be obtained. FIG. 6C shows an interference tomographic signal obtained by applying DC subtraction to the signals shown in FIGS. 6A and 6B using a signal after correction. In the interference signal tomographic image shown in FIG. 6C, only the interference signal 206 of the examined object appears, and noises have been removed. FIG. 7 shows an example of a tomographic image of the eye fundus in the case shown in FIGS. 6A to 6C. In this mode, what is important is that the reflecting means be arranged in such a way that the fixed pattern noise appears outside the tomographic image display area shown in FIG. 7.

Two or more of the features of the above-described modifications may be employed in combination, if feasible.

Second Embodiment

Figure 8:
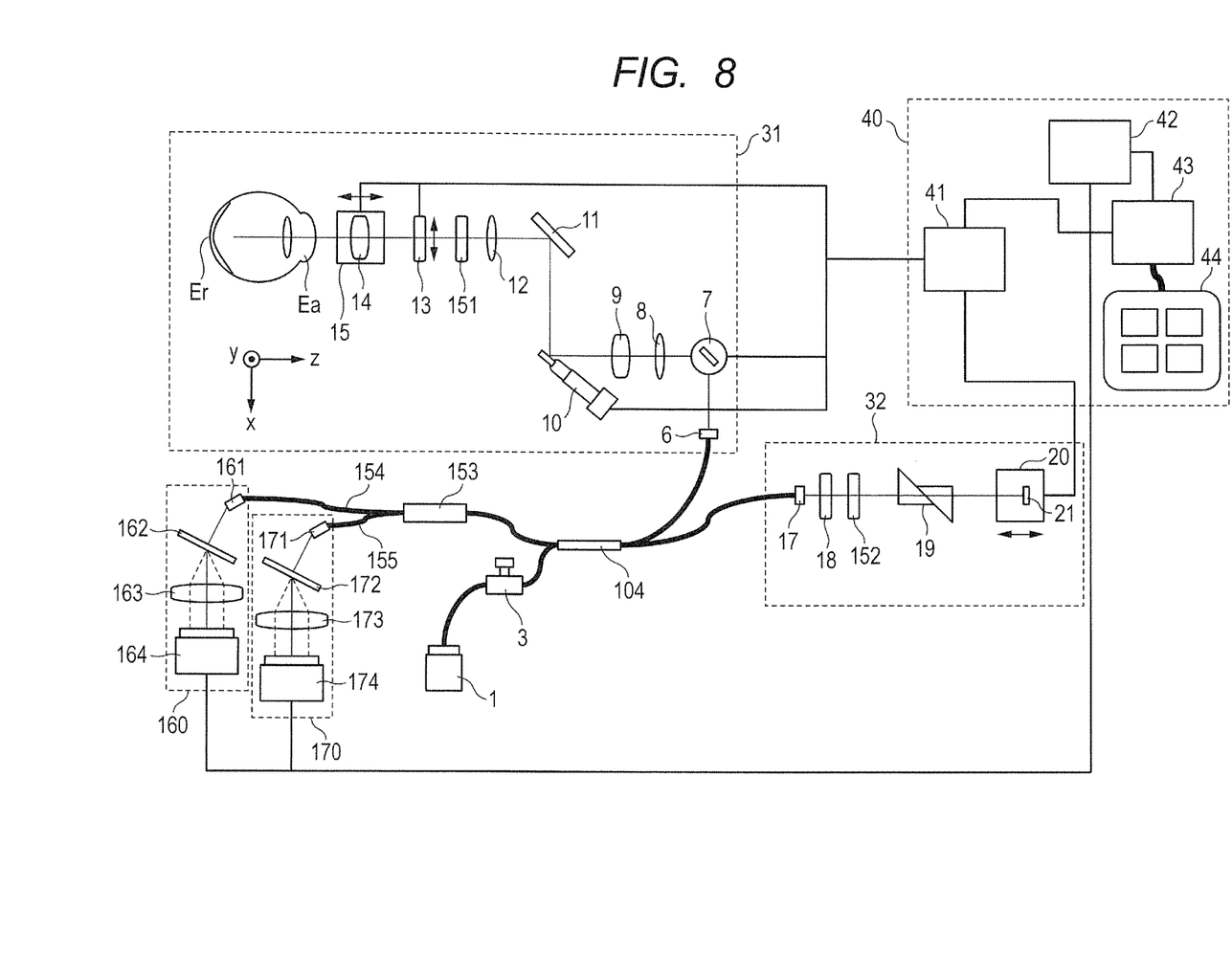
FIG. 8 is a diagram schematically illustrating the overall configuration of an image processing apparatus in a second embodiment of the present invention.

A second embodiment of the present invention will be described. FIG. 8 shows the general configuration of an optical coherence tomography image capturing apparatus (OCT apparatus) according to the second embodiment of the present invention. In this embodiment, a polarization sensitive OCT apparatus is used. The components and features that are the same as those in the first embodiment will not be described further, and only different components and features will be described.

The polarization of light emitted from the light source 1 is controlled by a polarization controller 3 serving as a polarization control unit and changed into linear polarization oriented in the vertical direction. The light after the polarization control is split by a polarization maintaining fiber coupler 104 serving as a polarization splitter into measurement light and reference light as polarization components perpendicular to each other. The polarization of the measurement light is converted from linear polarization into circular polarization by a quarter wave plate 151 provided on the optical axis of the measurement light in the sample arm 31, and the measurement light is delivered to the examined object (eye fundus Er). The measured light is reflected by the examined object while being affected by polarization characteristics of the examined object and returns to the polarization maintaining fiber coupler 104. The polarization of the reference light is converted from linear polarization oriented in the vertical direction into linear polarization at an angle of 45° by a quarter wave plate 152 provided on the optical axis of the reference light in the reference arm 32, and the reference light returns to the polarization maintaining fiber coupler 104. The measurement light and the reference light returning to the polarization maintaining fiber coupler 104 are combined to form interference light. The interference light is split by a polarization beam splitter 153 into polarization components perpendicular to each other. The polarization components thus split will be referred to as the horizontal component and the vertical component respectively. The polarization components after splitting are guided to spectrometers 160 and 170 respectively through fibers 154 and 155. Thus, in this embodiment, the same number of interference signal detection units as the number of measurement light after polarization splitting are provided so that interference signals can be detected for the respective polarization components. Therefore, the noise signal acquiring units are also provided for the respective polarization components so that noise signals can be acquired for the respective polarization components. In the spectrometers 160 and 170, interference light having passed through collimators 161 and 171 respectively is separated into spectral components by gratings 162 and 172 respectively, transmitted through lenses 163 and 173 respectively, and received by line cameras 164 and 174 respectively. The light received by the line cameras 164 and 174 is converted into electrical signals representing the light intensities of the respective polarization components and output from the line cameras 164 and 174. The output electrical signals are received by a signal processing unit 42. In the signal processing unit 42, polarization parameters (i.e. retardation and orientation) are obtained from the intensity and phase difference of tomographic signals generated by Fourier-transforming the polarization components.

Removal of fixed pattern noise in the second embodiment of the present invention will be described. In this embodiment, an FPN signal and an interference signal are acquired for each of the two orthogonal polarization components (horizontal component and vertical component). A correction coefficient is determined for each of the horizontal and vertical components, and correction and DC subtraction are performed in the same manner as in the first embodiment. Since correction and DC subtraction are performed for each of the polarization components, fixed pattern noises can be removed, even if the fixed pattern noises vary among the polarization components.

In the following other embodiments will be described. In the first embodiment, the intensity of one of the interference signal and the FPN signal is matched to the other signal. The present invention is not limited to this mode. Instead of matching the intensity of one signal to the other, the interference signal and the FPN signal may be normalized to a predetermined intensity. For the purpose of this normalization, the intensity of an interference signal and fixed pattern noises may be obtained and memorized in advance using as an examined object a measurement object (such as an model eye or reflecting mirror) serving as a substitution for an eye, and the intensity and the fixed pattern noises thus obtained and memorized may be used as the standard of normalization. In the case of this mode, comparison between both signals can be made at the same or substantially the same display bright ness, even if the light quantity of the OCT apparatus varies.

The apparatus to which the present invention can be applied is not limited to the main body of the OCT apparatus. The present invention can also be applied to removal of noise in optical interference image data. For example, noise removal may be performed by a processing apparatus separated from the OCT apparatus.

In the case where noise removal is performed by a processing apparatus separated from the OCT apparatus, an FPN signal may be generated by averaging interference signals. In this mode, an FPN signal can be generated from optical interference image data that does not contain an FPN signal, and noise removal according to the present invention can be performed on such image data.

The present invention is not limited to the apparatuses of the above-described embodiments. For example, the present invention may be implemented as a program that causes a computer to execute signal processing according to the above-described noise removal method.

While typical embodiments of the present invention have been described, the present invention is not limited to the above-described embodiments illustrated in the drawings. Various modifications can be made without deviating from the essence of the present invention. While SD-OCT has been described by way of example, the present invention can also be applied, for example, to SS-OCT.

The above-described embodiments enable removal of fixed pattern noises even when the brightness varies during measurement. Therefore, stable images can be obtained.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-206374, filed Oct. 7, 2014, which is hereby incorporated by reference herein in its entirety.

What is claimed is:

1. An image capturing apparatus comprising:
   a light splitter that splits light emitted from a light source into reference light and measurement light;
   a signal detector that acquires an interference signal from interference light resulting from interference of the reference light and return light generated by irradiating an object to be inspected with the measurement light, and that acquires a noise signal containing a noise component contained in the interference light; and
   a signal processor configured to:
   correct the intensity of one of the interference signal and the noise signal; and
   remove the noise component contained in the interference signal using the interference signal and the noise signal one of which is corrected.

2. An image capturing apparatus according to claim 1, wherein the signal processor Fourier-transforms the interference signal and the noise signal into an interference tomographic signal and a noise tomographic signal respectively and determines a depth position corresponding to a noise component from the noise tomographic signal, wherein a correction coefficient used in the correction is determined based on the intensities of noise components respectively in the interference tomographic signal and the noise tomographic signal corresponding to the depth position determined by the signal processor.

3. An image capturing apparatus according to claim 2, wherein when the noise signal contains a plurality of noise components, the signal processor determines correction coefficients for the respective noise components, and determines the correction coefficient used in the correction based on the correction coefficients for the respective noise components.

4. An image capturing apparatus according to claim 2, wherein when the noise signal contains a plurality of noise components, the unit signal processor determines correction coefficients for the respective noise components, and performs the correction for each of the noise components.

5. An image capturing apparatus according to claim 2, wherein when the noise signal contains a plurality of noise components and the signal processor determines correction coefficients for the respective noise components, if one or more of the correction coefficients thus determined exceed a predetermined threshold, the signal processor excludes the correction coefficients exceeding the threshold from the correction coefficients used in the correction.

6. An image capturing apparatus according to claim 5, wherein the threshold is a value set based on the change in the light quantity of the noise signal.

7. An image capturing apparatus according to claim 5, wherein the threshold is a value set based on the largest change in the light quantity of the noise signal.

8. An image capturing apparatus according to claim 2, further comprising a mirror provided in an optical path of the image capturing apparatus to reflect a portion of the light, wherein the signal detector acquires a noise component that can be detected when a tomographic image of the examined object is acquired and is generated by the mirror outside a display area in which the tomographic image is displayed, and the signal processor determines the correction coefficient used in the correction, based on the intensities of the noise signal and the interference signal on which the noise component thus generated is superposed.

9. An image capturing apparatus according to claim 2, wherein the signal processor performs the correction of the noise signal in accordance with the intensity of the noise component contained in the interference signal.

10. An image capturing apparatus according to claim 2, wherein the correction of the noise tomographic signal is performed in accordance with the intensity of the noise component contained in the interference signal.

11. An image capturing apparatus according to claim 2, wherein the signal processor performs the correction of the interference signal in accordance with the intensity of the noise component contained in the noise signal.

12. An image capturing apparatus according to claim 2, wherein the correction of the interference tomographic signal is performed in accordance with the intensity of the noise component contained in the noise signal.

13. An image capturing apparatus according to claim 2, further comprising a shutter assembly including a drive controller and a shutter that shuts off the measurement light travelling to the signal detector, wherein the signal detector acquires the noise signal in a state in which the measurement light is shut off by the shutter assembly.

14. An image capturing apparatus according to claim 13, wherein the shutter is inserted into the optical path of the measurement light.

15. An image capturing apparatus according to claim 13, wherein the shutter assembly includes a mirror provided in the optical path of the measurement light to direct the measurement light away from the object to be inspected, thereby preventing the measurement light from being detected by the signal detector.

16. An image capturing apparatus according to claim 2, wherein the signal detector acquires the noise signal by averaging a plurality of interference signals for forming a tomographic image of the examined object.

17. An image capturing apparatus according to claim 2, wherein when a plurality of tomographic images of the object to be inspected are generated, the signal processor determines a correction coefficient used to correct the intensities of noise components contained in the noise signal and the interference signal in correspondence with each other, for each of the tomographic images and performs the correction for each of the tomographic images.

18. An image capturing apparatus according to claim 2, further comprising:
　a polarization controller that controls the polarization of light emitted from the light source; and
　a polarization splitter that splits the light into polarization components perpendicular to each other,
　wherein the signal detector is arranged in such a way as to be capable of detecting the interference signal for each of the polarization components,
　the signal detector is arranged in such a way as to be capable of acquiring the noise signal for each of the polarization components,
　the signal processor corrects the intensity of one of the interference signal and the noise signal for each of the polarization components, and
　the signal processor removes the noise component contained in the interference signal using the interference signal and the noise signal one of which is corrected.

19. An image capturing apparatus according to claim 2, wherein the correction coefficient is obtained by dividing the intensity of the interference signal by the intensity of the noise signal.

20. An image capturing apparatus according to claim 19, wherein a corrected noise component is obtained by multiplying the noise signal by the correction coefficient, and subtracting the corrected noise component from the interference signal.

21. An image capturing apparatus according to claim 19, wherein a corrected interference signal is obtained by multiplying the interference signal by an inversion number of the correction coefficient, and subtracting the noise signal from the corrected interference signal.

* * * * *